(12) United States Patent  
Sato et al.

(10) Patent No.: US 10,939,888 B2  
(45) Date of Patent: Mar. 9, 2021

(54) RADIATION IRRADIATING APPARATUS

(71) Applicant: FUJIFILM Corporation, Tokyo (JP)

(72) Inventors: Masaru Sato, Kanagawa (JP); Kenji Nakamura, Kanagawa (JP); Misaki Kawahara, Kanagawa (JP); Fumito Nariyuki, Kanagawa (JP); Ryosuke Ogura, Kanagawa (JP); Tomoaki Nakashima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 67 days.

(21) Appl. No.: 16/550,305

(22) Filed: Aug. 26, 2019

(65) Prior Publication Data

US 2019/0380671 A1 Dec. 19, 2019

Related U.S. Application Data

(63) Continuation of application No. PCT/JP2017/038362, filed on Oct. 24, 2017.

(30) Foreign Application Priority Data

Feb. 28, 2017 (JP) .............................. JP2017-037297

(51) Int. Cl.
*G21K 5/00* (2006.01)
*H05G 1/10* (2006.01)
(Continued)

(52) U.S. Cl.
CPC .............. *A61B 6/54* (2013.01); *A61B 6/4405* (2013.01); *H05G 1/02* (2013.01); *H05G 1/10* (2013.01); *H05G 1/56* (2013.01)

(58) Field of Classification Search
CPC ........... A61N 2005/105; A61N 5/1049; G21K 1/025; H05G 1/02; H05G 1/10; H05G 1/265; H05G 1/32; H05G 1/54; H05G 1/56; H05G 1/30; H05G 1/34; H05G 1/38; H05G 1/40; A61B 6/4405; A61B 6/56;
(Continued)

(56) References Cited

U.S. PATENT DOCUMENTS 9,521,986 B2    12/2016  Ozawa et al.
10,368,826 B2 *  8/2019  Tamura ................ A61B 6/4233
(Continued)

FOREIGN PATENT DOCUMENTS

JP    S63287935     11/1988
JP    2004340479    12/2004
(Continued)

OTHER PUBLICATIONS

"Office Action of Japan Counterpart Application," with English translation thereof, dated Jan. 21, 2020, p. 1-p. 8.
(Continued)

*Primary Examiner* — Irakli Kiknadze
(74) *Attorney, Agent, or Firm* — JCIPRNET

(57) ABSTRACT

A radiation irradiating apparatus includes a radiation generator that generates radiation and a switch that controls emission of the radiation from the radiation generator. The radiation generator and the switch are constituted by separate housings. The radiation generator and the switch are attachable and detachable to and from each other via a surface of a portion of each of the housings thereof.

15 Claims, 6 Drawing Sheets

(51) Int. Cl.
*A61B 6/00* (2006.01)
*H05G 1/02* (2006.01)
*H05G 1/56* (2006.01)

(58) Field of Classification Search
CPC .. A61B 6/467; A61B 6/00; A61B 6/02; A61B 6/102; A61B 6/4021; A61B 6/461; A61B 6/54; A61B 6/548; A61B 2560/0223; A61B 5/1114; A61B 5/4528; A61B 6/04; A61B 6/06; A61B 6/14; A61B 6/4014; A61B 6/542; A61B 6/40; A61B 6/4266; A61B 6/08; A61B 6/107; A61B 6/4291; A61B 6/4452; A61B 6/4464; A61B 6/484; A61B 6/588; A61B 6/4007; A61B 6/42; A61B 6/4208; A61B 6/4233; A61B 6/4283; A61B 6/4411; A61B 6/4441; A61B 6/465; A61B 6/563; A61B 6/566; H01J 35/06; H01J 35/025; H01J 35/065; H01J 35/14; H01J 35/02; H01J 35/045; H01J 35/066; H01J 35/147; H01J 35/153; H01J 35/30; H01J 35/00; H01J 35/064; H01J 35/101; H01J 35/24; H01J 2201/30469; H01J 2235/068; H01J 2235/1026; H01J 2235/1204; H01J 2235/1262; H01J 2235/127; G01N 23/04; G01N 2223/301; Y10T 29/49002; Y10T 29/5313; G01V 5/0041; H02H 9/005
USPC ............... 378/62, 64, 91, 101–103, 114, 117
See application file for complete search history.

(56) References Cited

U.S. PATENT DOCUMENTS

| | | | | |
|---|---|---|---|---|
| 10,610,187 | B2 * | 4/2020 | Takeshima | ............... A61B 6/54 |
| 2001/0038248 | A1 * | 11/2001 | Yagi | ............... H05G 1/02 307/328 |
| 2007/0269010 | A1 * | 11/2007 | Turner | ............... H05G 1/10 378/102 |
| 2008/0075233 | A1 * | 3/2008 | Coombs | ............... A61B 6/4405 378/204 |
| 2011/0049370 | A1 | 3/2011 | Yoshida | |
| 2011/0286578 | A1 * | 11/2011 | Butzine | ............... A61B 6/4405 378/98.5 |
| 2011/0317816 | A1 * | 12/2011 | Bechard | ............... A61B 6/56 378/98.8 |
| 2013/0214157 | A1 | 8/2013 | Kitano | |
| 2013/0279661 | A1 | 10/2013 | Tamura et al. | |
| 2015/0313570 | A1 * | 11/2015 | Han | ............... H01H 36/008 378/62 |

FOREIGN PATENT DOCUMENTS

| | | |
|---|---|---|
| JP | 2010014877 | 1/2010 |
| JP | 2011030686 | 2/2011 |
| JP | 2011045439 | 3/2011 |
| JP | 2012073768 | 4/2012 |
| JP | 2013039248 | 2/2013 |
| JP | 2013225380 | 10/2013 |
| JP | 2014204783 | 10/2014 |
| JP | 2015054178 | 3/2015 |
| JP | 2017006345 | 1/2017 |
| WO | 2007034597 | 3/2007 |

OTHER PUBLICATIONS

"International Search Report (Form PCT/ISA/210) of PCT/JP2017/038362," dated Dec. 19, 2017, with English translation thereof, pp. 1-4.

"Written Opinion of the International Searching Authority (Form PCT/ISA/237) of PCT/JP2017/038362," dated Dec. 19, 2017, with English translation thereof, pp. 1-7.

* cited by examiner

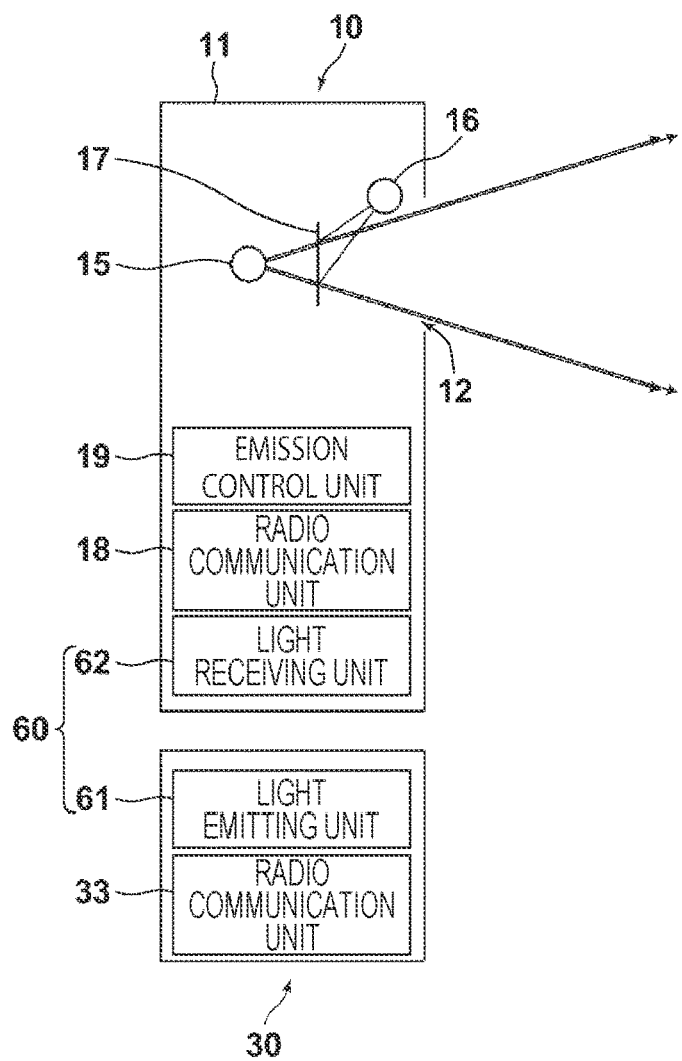
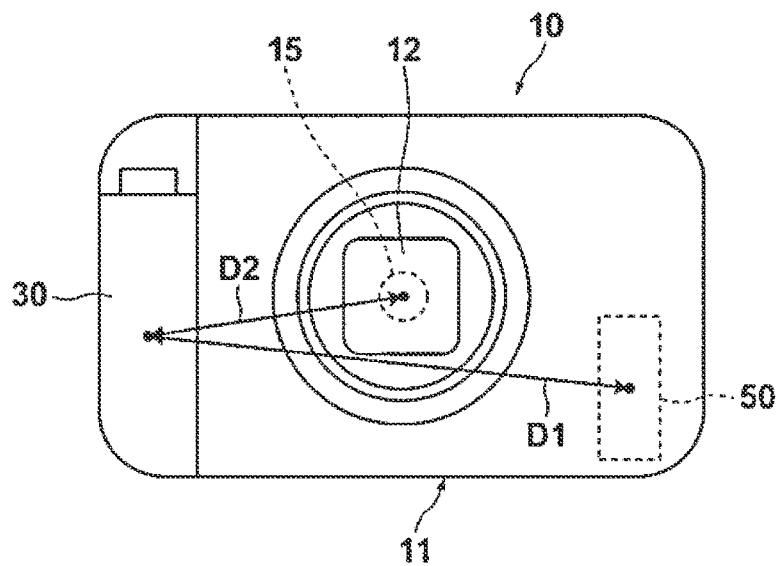

RADIATION IRRADIATING APPARATUS

CROSS-REFERENCE TO RELATED APPLICATION

The present application is a Continuation of PCT International Application No. PCT/JP2017/038362 filed on Oct. 24, 2017, which claims priority under 35 U.S.C. § 119(a) to Japanese Patent Application No. 2017-037297 filed on Feb. 28, 2017. Each of the above applications is hereby expressly incorporated by reference, in its entirety, into the present application.

BACKGROUND

Technical Field

The present disclosure relates to a radiation irradiating apparatus for use in radiography and relates, in particular, to a portable radiation irradiating apparatus.

Description of the Related Art

Various carriable (portable) radiation irradiating apparatuses for use at home or in disaster areas and the like have been proposed.

Such a carriable radiation irradiating apparatus includes an exposing switch for controlling exposure of radiation. In general, an exposing switch is configured, as an independent unit, separately from a radiation irradiating apparatus main body having a radiation generator. For example, JP2015-54178A discloses a feature in which an exposing switch and a radiation irradiating apparatus main body communicate with each other via wire or wireless and in which the radiation irradiating apparatus main body is caused to emit radiation in response to depression of the exposing switch.

SUMMARY

It is however not possible to integrally carry the radiation irradiating apparatus main body and the exposing switch when, as described above, the exposing switch is provided as an independent unit separately from the radiation irradiating apparatus main body. Thus, there is the possibility of the exposing switch being misplaced and unusable at an actual photographing location.

In addition, there is the possibility of the exposing switch being dropped and broken during carrying of the radiation irradiating apparatus and during setting of the radiation irradiating apparatus at an actual location.

It may be considered to, for example, dispose a hook mechanism or the like on the radiation irradiating apparatus main body and to hook the exposing switch on the hook mechanism and carry the exposing switch together with the radiation irradiating apparatus main body; however, there is still the possibility of the exposing switch being dropped and broken as a result of a trouble in hooking the exposing switch on the hook mechanism or as a result of a failure in hooking thereof. In some configurations of the hook mechanism, the exposing switch is hooked on the hook mechanism in an unstable state and may be dropped.

Considering the aforementioned issues, the present disclosure provides a radiation irradiating apparatus that enables an exposing switch to be integrally carried together with a radiation irradiating apparatus main body having a radiation generator and that enables the exposing switch to be easily attachable/detachable with respect to the radiation irradiating apparatus main body.

A radiation irradiating apparatus according to the present disclosure includes a radiation generator that generates radiation and a switch that controls emission of the radiation from the radiation generator. The radiation generator and the switch are constituted by separate housings. The radiation generator and the switch are attachable and detachable to and from each other via a surface of a portion of each of the housings thereof.

In the aforementioned radiation irradiating apparatus according to the present disclosure, a concave section may be disposed in the housing of the radiation generator, and a surface forming the concave section and a surface of a portion of the housing of the switch may each constitute an attaching/detaching surface.

In the aforementioned radiation irradiating apparatus according to the present disclosure, the attaching/detaching surface of the switch can have two surfaces orthogonal to each other.

In the aforementioned radiation irradiating apparatus according to the present disclosure, the attaching/detaching surfaces of the radiation generator and the switch may be curved surfaces.

In the aforementioned radiation irradiating apparatus according to the present disclosure, the radiation generator and the switch may be attachable and detachable to and from each other via only one surface of each of the housings thereof.

In the aforementioned radiation irradiating apparatus according to the present disclosure, when the switch is attached to the radiation generator, a surface of the housing of the switch, the surface being other than the attaching/detaching surface, can be flush with a housing surface of the radiation generator.

In the aforementioned radiation irradiating apparatus according to the present disclosure, at least two mutually orthogonal surfaces of the housing of the switch, the at least two mutually orthogonal surfaces being other than the attaching/detaching surface, can be flush with housing surfaces of the radiation generator.

In the aforementioned radiation irradiating apparatus according to the present disclosure, the housing of the switch may form a portion of a surface of a rectangular parallelepiped or a corner thereof in a state in which the switch is attached to the radiation generator.

In the aforementioned radiation irradiating apparatus according to the present disclosure, the radiation generator and the switch may be attachable and detachable to and from each other due to a magnet.

In the aforementioned radiation irradiating apparatus according to the present disclosure, the radiation generator and the switch may be attachable and detachable to and from each other due to a member having adhesiveness.

In the aforementioned radiation irradiating apparatus according to the present disclosure, the radiation generator and the switch may be attachable and detachable to and from each other due to a mechanical configuration.

In the aforementioned radiation irradiating apparatus according to the present disclosure, the radiation irradiating apparatus may include an emission control unit that stops emission of radiation from the radiation generator when the switch is attached to the radiation generator.

In the aforementioned radiation irradiating apparatus according to the present disclosure, the radiation irradiating apparatus may include a detection unit that detects that the switch is attached to the radiation generator.

In the aforementioned radiation irradiating apparatus according to the present disclosure, the detection unit may be disposed on each of the attaching/detaching surfaces of the radiation generator and the switch.

In the aforementioned radiation irradiating apparatus according to the present disclosure, the radiation generator may have a battery, and, when the switch is attached to the radiation generator, a distance from the switch to the battery may be longer than a distance from the switch to a radiation source of the radiation generator.

According to the radiation irradiation apparatus of the present disclosure, the radiation generator and the switch are attachable and detachable to and from each other via a surface of a portion of each of the housings thereof, which enables the switch to be integrally carried together with the radiation generator and enables the switch to be easily attachable and detachable with respect to the radiation generator. Moreover, due to the switch being attached with respect to the radiation generator via the surfaces, it is possible to attach the switch in a stable state, compared to the switch attached by being hooked on a hook mechanism or the like.

BRIEF DESCRIPTION OF THE DRAWINGS

Exemplary embodiments of the present invention will be described in detail based on the following figures, wherein:

FIG. 5 is a schematic view illustrating internal configurations of the radiation generator and the exposing switch;

FIG. 6 describes a distance relationship between the exposing switch and the battery;

DETAILED DESCRIPTION

Figure 1:
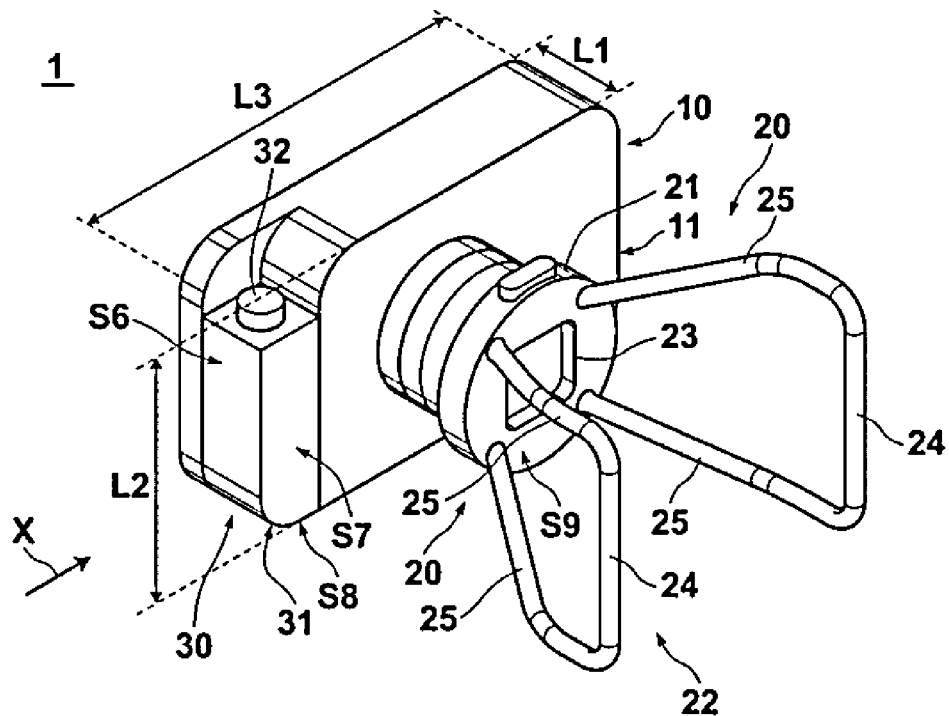
FIG. 1 is a perspective view illustrating an external configuration of an embodiment of the radiation irradiating apparatus according to the present disclosure.
Figure 2:
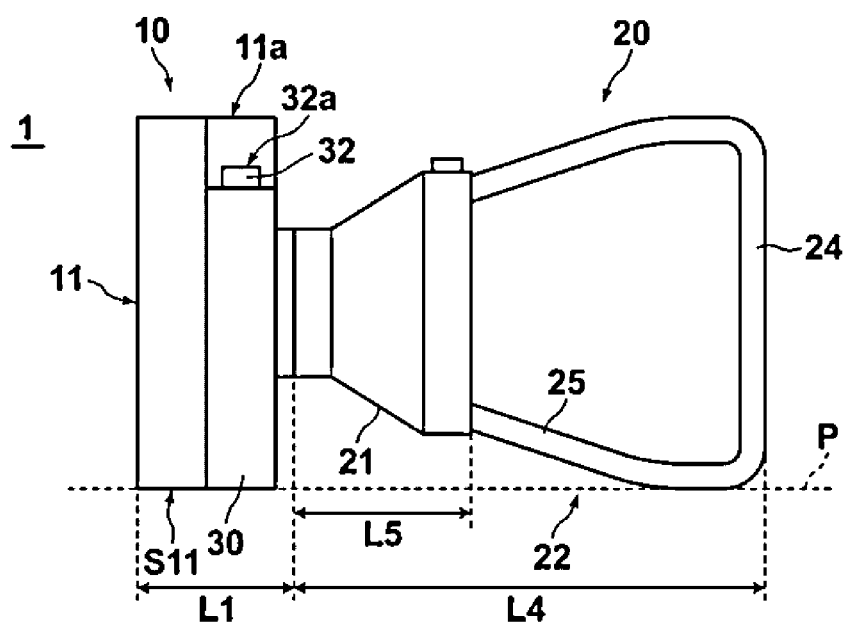
FIG. 2 is an external side view of the radiation irradiating apparatus illustrated in FIG. 1 as viewed in the arrow X direction.

Hereinafter, an embodiment of the radiation irradiating apparatus according to the present disclosure will be described in detail with reference to the drawings. The radiation irradiating apparatus according of the present embodiment is a carriable radiation irradiating apparatus for use mainly at home or in disaster areas and the like. FIG. 1 is a perspective view illustrating an external configuration of a radiation irradiating apparatus 1 of the present embodiment. FIG. 2 is an external side view of the radiation irradiating apparatus 1 illustrated in FIG. 1 as viewed in the arrow X direction.

As illustrated in FIG. 1, the radiation irradiating apparatus 1 of the present embodiment includes a radiation generator 10, a detachable portion 20, and an exposing switch 30 (corresponding to the switch of the present disclosure).

The radiation generator 10 includes a radiation source 15, such as an X-ray tube, that generates radiation. The radiation generator 10 emits radiation generated in the radiation source 15. The radiation generator 10 includes a housing 11, and the radiation source 15 and the like are accommodated in the housing 11. The housing 11 is formed to have a rectangular parallelepiped shape and configured such that a length L1 of a first side extending in an optical axis direction of radiation is shorter than a length L2 of a second side orthogonal to the first side and a length L3 of a third side. The relationship among the length L1 of the first side, the length L2 of the second side, and the length L3 of the third side is preferably L1<L2<L3. A ratio between the length L of the first side and the length L3 of the third side is preferably 1:1 to 1:6. A ratio between the length L1 of the first side and the length L2 of the second side is preferably 1:1 to 1:6. Setting the length of the housing 11 of the radiation generator 10 at the aforementioned ratio improves portability of the radiation irradiating apparatus 1 and userbility in the usage thereof. The length L1 of the first side is preferably 80 mm or less.

As illustrated in FIG. 2, a ratio between the length L1 of the first side of the housing 11 of the radiation generator 10 and a length L4 of the detachable portion 20 in the optical axis direction is preferably 1:1 to 1:4. Consequently, it is possible to downsize the radiation irradiating apparatus 1 and to assure a distance between the radiation generator 10 and a patient. A length L5 of a later-described collimator 21 of the detachable portion 20 in the optical axis direction is preferably no more than one-third of the length L1+L4 of the entirety of the radiation irradiating apparatus 1 in the optical axis direction.

Figure 3:
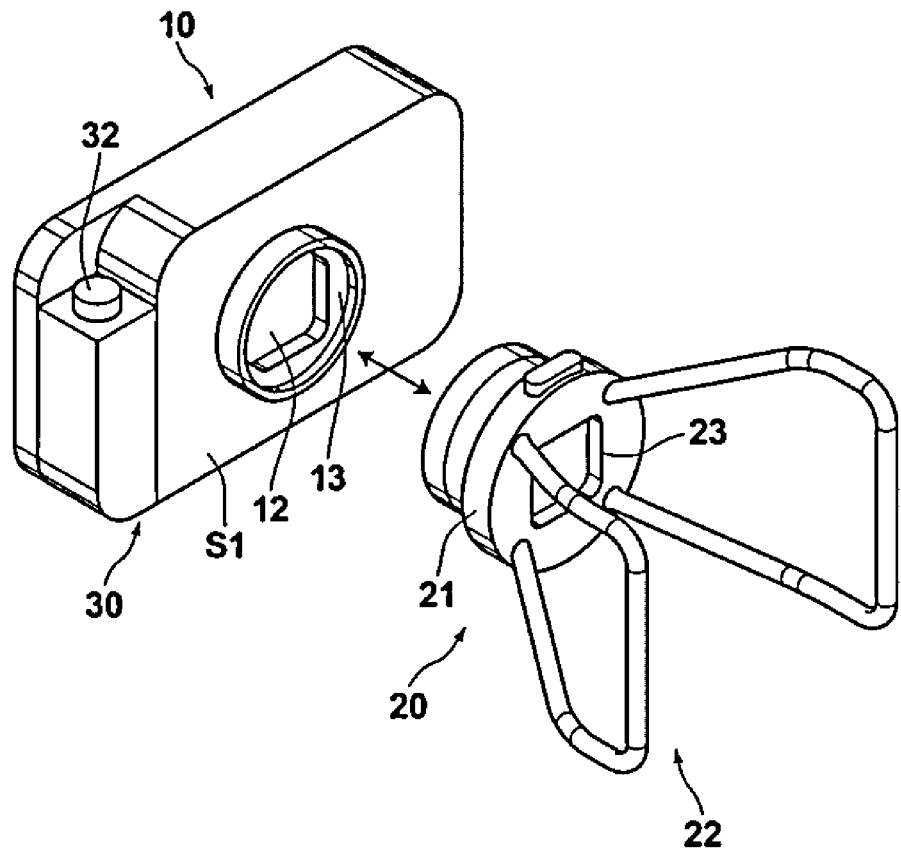
FIG. 3 illustrates a state in which a detachable portion is detached from a radiation generator of the radiation irradiating apparatus.

The radiation generator 10 and the detachable portion 20 of the radiation irradiating apparatus 1 are attachable/detachable as illustrated in FIG. 3 to and from each other. As illustrated in FIG. 3, a rectangular opening 12 through which radiation generated in the radiation source 15 is emitted is formed in a surface S1 of the housing 11 of the radiation generator 10. The opening 12 is preferably formed at a position at which the center of a rectangle defined by the second side and the third side, which are illustrated in FIG. 1, and the center of the opening 12 coincide with each other. Although the position of the opening 12 is not necessarily the aforementioned position, the center of the opening 12 is preferably set within a range of a circle having a radius of 60 mm from the center of the aforementioned rectangle.

An installation portion 13 at which the detachable portion 20 is detachably installed is formed at the periphery of the opening 12 of the housing 11. A magnet having a polarity opposite to the polarity of a magnet disposed at the detachable portion 20 is disposed at the installation portion 13. Due to the magnetic force of the magnet, the detachable portion 20 is attachable/detachable with respect to the installation portion 13.

Figure 4:
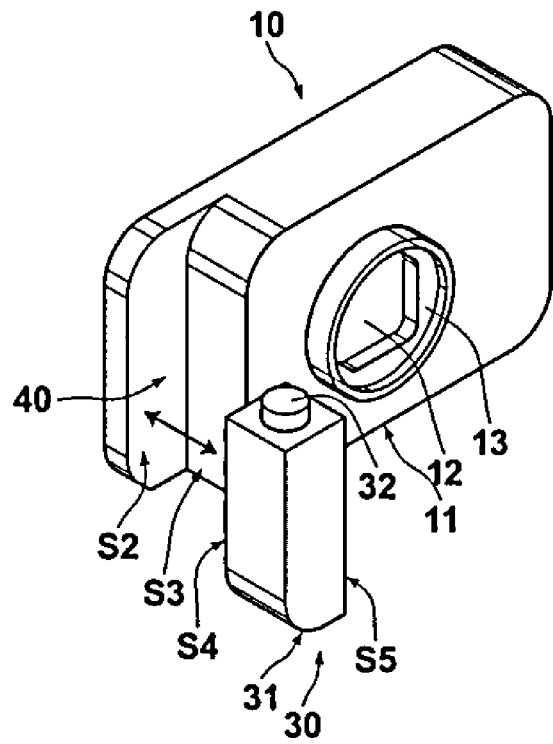
FIG. 4 illustrates a state in which an exposing switch is detached from the radiation generator.

As illustrated in FIG. 4, a concave section 40 is formed in the housing 11 of the radiation generator 10. The concave section 40 is formed by mutually orthogonal two surfaces S2 and S3 and is configured such that the exposing switch 30 is fitted into a space inside the concave section 40 formed by these two surfaces. The exposing switch 30 includes a housing 31, which differs from the housing of the radiation generator 10. The radiation generator 10 and the exposing switch 30 are attachable/detachable to and from each other via a portion of a surface of each of the housings thereof.

Specifically, the two surfaces S2 and S3 forming the concave section 40 of the housing 11 of the radiation generator 10 and mutually orthogonal two surfaces S4 and S5 of the housing 31 of the exposing switch 30 each constitute an attaching/detaching surface. The radiation generator 10 and the exposing switch 30 are attachable/detachable to and from each other via the attaching/detaching surfaces thereof.

A magnet is disposed in the vicinity of an inner surface on the rear side of each of the attaching/detaching surface of the radiation generator 10 and the attaching/detaching surface of the exposing switch 30, the magnets having opposite polarities. Due to the magnetic force of the magnets, the radiation generator 10 and the exposing switch 30 are attachable/detachable to and from each other.

As a result of the radiation generator 10 and the exposing switch 30 being attachable/detachable via the surface of a portion of each of the housings thereof, the exposing switch 30 can be integrally carried together with the radiation generator 10, and the exposing switch 30 can be easily attached and detached by one touch with respect to the radiation generator 10.

Due to the exposing switch 30 being attachable with respect to the radiation generator 10 via the attaching/detaching surfaces, it is possible to attach the exposing switch 30 in a stable state, compared to the exposing switch 30 attached by being hooked on a hook mechanism of the like.

Accordingly, a workflow of a user can be improved because the exposing switch 30 can be integrally handled together with the radiation generator 10 at a location of, for example, radiography at home. In the improved workflow, the exposing switch 30 is detached from the radiation generator 10 only when a final exposure is to be performed. Thus, it is possible to reduce the possibility of the exposing switch 30 being dropped by accident during setting of the radiation irradiating apparatus 1.

In the radiation irradiating apparatus 1 of the present embodiment, as illustrated in FIG. 1, surfaces S6, S7 and S8 of the housing 31 of the exposing switch 30, other than the aforementioned attaching/detaching surfaces S4 and S5, are flush with housing surfaces of the radiation generator 10 when the exposing switch 30 is attached to the radiation generator 10. Specifically, in the present embodiment, the mutually orthogonal three surfaces S6, S7, and S8, which are surfaces other than the attaching/detaching surfaces S4 and S5, of the housing 31 of the exposing switch 30 are flush with surfaces of the housing 11 of the radiation generator. The housing 31 of the exposing switch 30 constitutes a portion of surfaces of the rectangular parallelepiped and a corner thereof in a state in which the exposing switch 30 is attached to the radiation generator 10.

Due to such a configuration, unnecessary projections and the like are not present when the exposing switch 30 is attached to the radiation generator 10, which enables easy handling.

A button 32 is disposed at the exposing switch 30. When the button 32 is depressed, radiation is emitted from the radiation generator 10.

FIG. 5 is a schematic view illustrating internal configurations of the radiation generator 10 and the exposing switch 30. The aforementioned radiation source 15, a light source 16, and a mirror 17 are disposed in the housing 11 of the radiation generator 10. The mirror 17 transmits radiation generated in the radiation source 15 and reflects visible light emitted from the light source 16. The light source 16 is constituted by an LED (light emitting diode) and emits visible light. As illustrated in FIG. 5, the light source 16 is disposed on a side opposite the radiation source 15 side with respect to the mirror 17 and positioned outside an emission range of radiation emitted from the radiation source 15.

Radiation that is emitted from the radiation source 15 and transmitted through the mirror 17, and visible light that is emitted from the light source 16 and reflected by the mirror 17 are both emitted from the opening 12 of the housing 11.

Radio communication units 18 and 33 are disposed at the radiation generator 10 and the exposing switch 30, respectively. When the button 32 of the exposing switch 30 is depressed, a radio signal is output from the radio communication unit 33 of the exposing switch 30 toward the radiation generator 10, and the radio signal is received by the radio communication unit 18 of the radiation generator 10. When the radio signal output from the exposing switch 30 is received by the radio communication unit 18, an emission control unit 19 of the radiation generator 10 controls to cause the radiation source 15 to emit radiation.

The emission control unit 19 stops emission of radiation from the radiation generator 10 during a period in which the exposing switch 30 is attached to the radiation generator 10, even when the button 32 of the exposing switch 30 is depressed. Consequently, a so-called interlock function is included. In other words, if emission of radiation is enabled in a state in which the exposing switch 30 is attached to the radiation generator 10, there is the possibility of the button 32 being depressed by accident during carrying and setting-up of the radiation irradiating apparatus 1 and causing an accidental exposure. Such an accidental exposure is suppressed by including the aforementioned interlock function.

To achieve the aforementioned interlock function, the radiation irradiating apparatus 1 includes a detection unit 60 that detects that the exposing switch 30 is attached to the radiation generator 10. The radiation irradiating apparatus 1 of the present embodiment includes a photocoupler as the detection unit 60. Specifically, a light emitting unit 61 is disposed on the attaching/detaching surface of the exposing switch 30, and a light receiving unit 62 is disposed on the attaching/detaching surface of the radiation generator 10 opposite the aforementioned attaching/detaching surface of the exposing switch 30. As a result of light emitted from the light emitting unit 61 being received by the light receiving unit 62, it is detected that the exposing switch 30 is attached to the radiation generator 10.

In the present embodiment, the photocoupler is used as the detection unit 60; however, the detection unit 60 is not limited thereto and may be another proximity sensor, such as a magnetic sensor. Instead of using such a contactless sensor, a mechanical switch may be disposed to detect that the exposing switch 30 is attached to the radiation generator 10.

To suppress the button 32 of the exposing switch 30 from being depressed by accident, an upper surface 32a of the button 32 is preferably positioned, as illustrated in FIG. 2, on the lower side of an upper surface 11a of the housing 11 of the radiation generator 10. Note that, in the present specification, an upper side in the vertical direction and a lower side in the vertical direction in a state in which the exposing switch 30 is attached to the radiation generator 10 such that the button 32 faces the upper side in the vertical direction are referred to as "upper" and "lower", respectively.

As illustrated in FIG. 6, a battery 50 that has a storage battery, such as a lithium ion battery, a power supply circuit, and the like is disposed in the housing 11 of the radiation generator 10. To suppress the exposing switch 30 from malfunctioning due to a noise generated from the power supply circuit of the battery 50, the distance between the exposing switch 30 and the battery 50 is preferably set to a longest possible distance. Specifically, it is preferable that a distance D1 from the exposing switch 30 to the battery 50 be longer than a distance D2 from the exposing switch 30 to the radiation source 15 of the radiation generator 10 when the exposing switch 30 is attached to the radiation generator 10. The radiation source 15 is disposed in the vicinity of the center of the housing 11 of the radiation generator 10.

Next, the detachable portion 20 will be described. As illustrated in FIG. 1 to FIG. 3, the detachable portion 20 is the collimator 21 and a distance assuring portion 22 that are integrally formed. In other words, the collimator 21 and the distance assuring portion 22 form an integral structure to constitute the detachable portion 20. A magnet having a polarity opposite to the polarity of the magnet disposed at the installation portion 13 of the radiation generator 10 is disposed at the collimator 21. As described above, due to the magnetic force of the magnet, the detachable portion 20 is attachable/detachable with respect to the installation portion 13.

The collimator 21 is configured to control an irradiation range of radiation generated in the radiation generator 10. The collimator 21 includes a stop (not illustrated) and controls the irradiation range of radiation that a patient is irradiated with by changing the size of the stop. The size of the stop is manually changeable by a user. As illustrated in FIG. 1 and FIG. 3, a rectangular emission port 23 is disposed in the collimator 21, and radiation that has passed through an opening of the stop is emitted from the emission port 23.

As illustrated in FIG. 1, the distance assuring portion 22 has abutting members 24 that abut on a patient (subject) to be irradiated with radiation, when the radiation generator 10 and the patient approach each other such that a distance therebetween is smaller than a preset distance. As a result of the abutting members 24 abutting on the patient, a distance between the radiation generator 10 and the patient is assured.

The distance assuring portion 22 includes four columnar members 25 extending from a surface S9 of the housing of the collimator 21 on the radiation emitting side in a radiation emitting direction, and the aforementioned two abutting members 24 each connected between tip portions of a pair of the columnar members 25 corresponding thereto.

Figure 7:
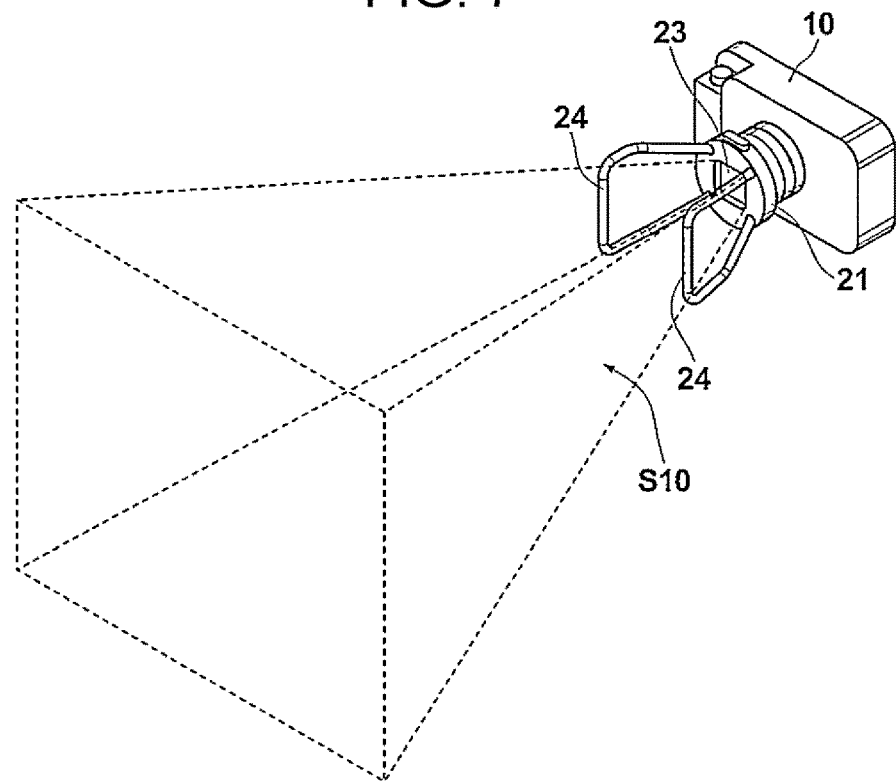
FIG. 7 describes an arrangement of an abutting member.
Figure 8A:
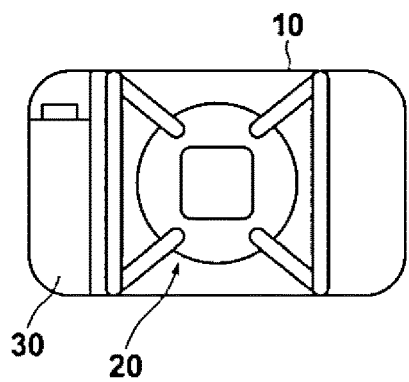
FIGS. 8A, 8B, 8C, and 8D illustrate states of the detachable portion attached to the radiation generator at various angles.
Figure 8B:
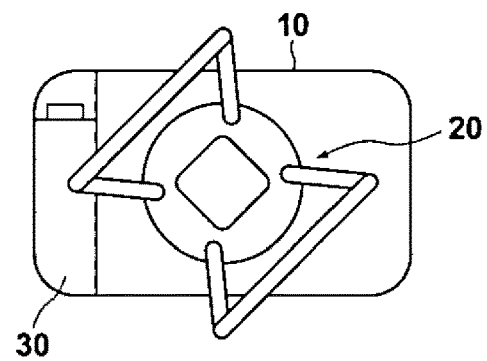
Figure 8C:
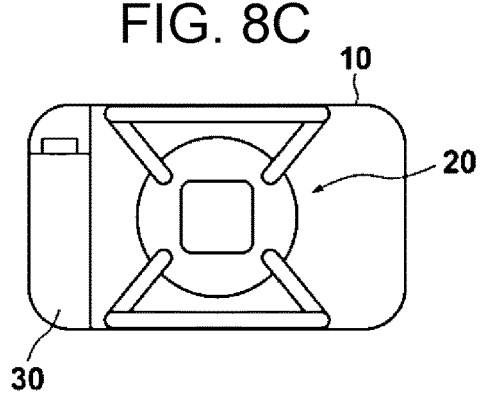
Figure 8D:
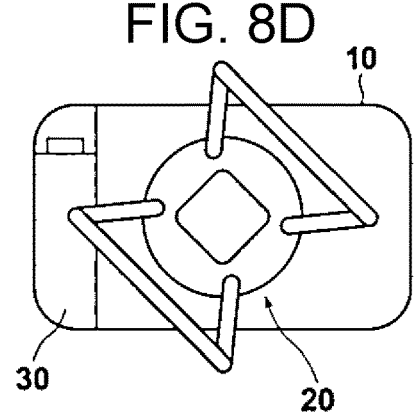

As illustrated in FIG. 1, the four columnar members 25 are formed such that a distance therebetween increases from the surface S9 of the collimator 21 on the radiation emitting side toward a patient side. As illustrated in FIG. 7, the abutting members 24 are positioned in contact with a surface S10 that is formed by connecting an edge of the opening 12 (refer to FIG. 3) of the radiation generator 10 and an edge of the opening of the stop of the collimator 21 when the stop has a maximum size. Such a configuration enables a rectangular range formed by four end portions of the two abutting members 24 to be identical to the irradiation range of radiation and thus to have a minimum necessary size, which enables downsizing of the detachable portion 20.

The columnar members 25 are preferably disposed, as illustrated in FIG. 2, on a plane P that is formed by extending a lower surface S11 of the housing 11 of the radiation generator 10 in the optical axis direction of radiation. Consequently, when the radiation irradiating apparatus 1 is disposed on a predetermined plane, a portion of the columnar members 25 comes into contact with the plane, and the radiation irradiating apparatus 1 is thereby supported, which suppresses the radiation irradiating apparatus 1 from falling down.

FIGS. 8A to 8D illustrate four states of the detachable portion 20 attached to the radiation generator 10. In the present embodiment, as described above, the detachable portion 20 is attachable/detachable with respect to the radiation generator 10 due to the magnets. Accordingly, as illustrated in FIGS. 8A to 8D, the detachable portion 20 is attachable by being rotated at a freely selected angle around an axis passing the center of the stop of the collimator 21 and extending in the optical axis direction of radiation. Such a configuration enables easy attachment/detachment of the detachable portion 20 with respect to the radiation generator 10. In addition, as a result of the collimator 21 being rotatable, the irradiation range of radiation can be changed depending on a photographing portion of a patient, which improves operability.

The radiation irradiating apparatus 1 of the present embodiment is configured such that the centroid position of the entirety of the radiation irradiating apparatus 1 is on the side of the radiation generator 10 when the detachable portion 20 is attached to the radiation generator 10. The thus adjusted centroid position suppresses the radiation irradiating apparatus 1 from easily falling down. In the present embodiment, as described above, the light source 16 and the mirror 17 are disposed on the side of the radiation generator 10, and therefore, the above-described adjustment of the centroid position is easily performed.

Emission of radiation from the radiation generator 10 may be stopped by the emission control unit 19 when the detachable portion 20 is detached from the radiation generator 10. Consequently, an interlock function can be included, and careless emission of radiation from the radiation generator 10 is suppressed, and safety can be assured. To detect attachment/detachment of the detachable portion 20 with respect to the radiation generator 10, for example, an optical sensor, such as a photocoupler, and a proximity sensor, such as a magnetic sensor, may be disposed, or a mechanical switch may be disposed.

In the aforementioned embodiment, the magnets are used to configure such that the exposing switch 30 and the radiation generator 10 can be attached/detached to and from each other; however, the attachable/detachable configuration is not limited thereto. A mechanical mechanism may be employed to provide the attachable/detachable configuration. FIG. 9 to FIG. 12 illustrate examples of an attachable/detachable configuration using a mechanical mechanism and each illustrate the radiation generator 10 illustrated in FIG. 1 as viewed in the arrow X direction.

Figure 9:
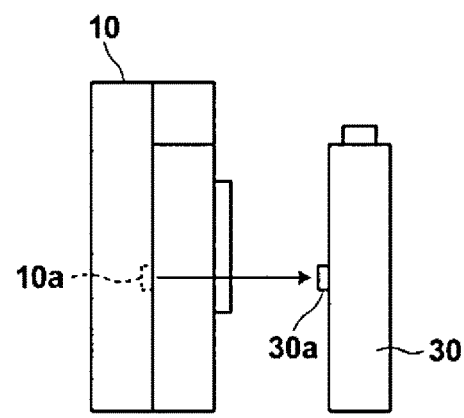
FIG. 9 illustrates another detachable mechanism of the radiation generator and the exposing switch.

Specifically, as illustrated for example in FIG. 9, a button 30a may be disposed on the attaching/detaching surface of the exposing switch 30, and a hole 10a into which the button 30a is detachably fitted may be disposed on the attaching/detaching surface of the radiation generator 10 to thereby provide an attachable/detachable configuration using a button mechanism.

Figure 10:
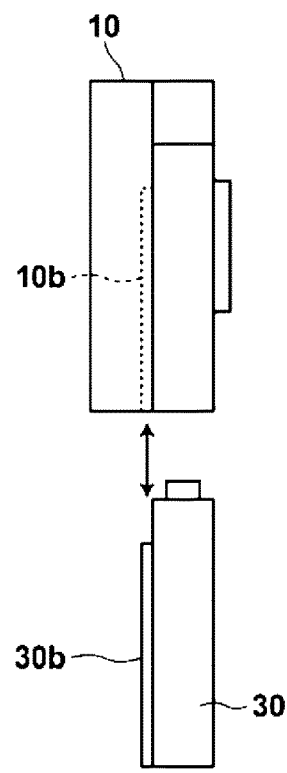
FIG. 10 illustrates another detachable mechanism of the radiation generator and the exposing switch.

Moreover, as illustrated in FIG. 10, a groove 10b may be formed on the attaching/detaching surface of the radiation generator 10, and a projection 30b that is detachably fitted into the groove 10b may be disposed on the attaching/detaching surface of the exposing switch 30 to thereby provide an attachable/detachable configuration using an insertion mechanism.

Figure 11:
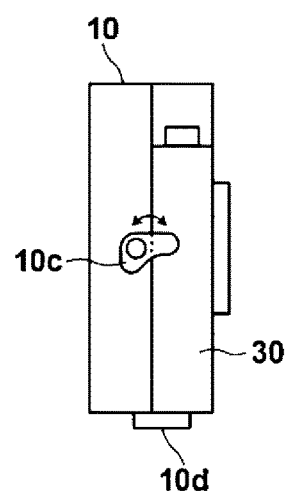
FIG. 11 illustrates another detachable mechanism of the radiation generator and the exposing switch.

Further, as illustrated in FIG. 11, lock members 10c and 10d that rotate in the arrow direction may be disposed on the housing surfaces of the radiation generator 10 to thereby provide an attachable/detachable configuration using the lock members 10c and 10d to support the exposing switch 30. The lock member 10d illustrated in FIG. 11 has a configuration identical to the configuration of the lock member 10c and differs from the lock member 10c only in terms of attachment surface.

Figure 12:
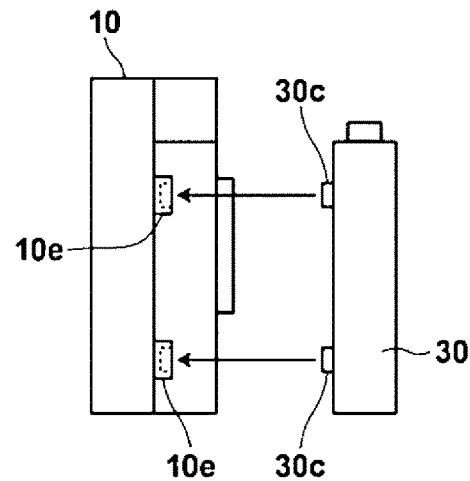
FIG. 12 illustrates another detachable mechanism of the radiation generator and the exposing switch.

Furthermore, as illustrated in FIG. 12, female portions 10e may be disposed on the attaching/detaching surface of the radiation generator 10, and male portions 30c that are detachably fitted into concave sections of the female portions 10e may be disposed on the attaching/detaching surface of the exposing switch 30 to thereby provide an attachable/detachable configuration using an insertion mechanism.

In the aforementioned embodiment, the magnets are used to configure such that the radiation generator 10 and the exposing switch 30 can be attached/detached to and from each other, however, the attachable/detachable configuration may be provided by disposing a member having adhesiveness on each of the attaching/detaching surface of the radiation generator 10 and the attaching/detaching surface of the exposing switch 30. As the member having adhesiveness, a hook-and-loop fastener (for example, a magic tape (registered trademark)) may be used, or an adhesive tape having adhesiveness may be used.

Figure 13:
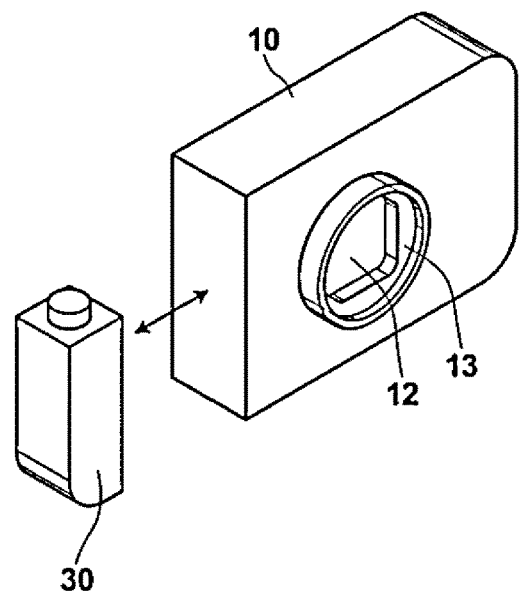
FIG. 13 illustrates a configuration in which the radiation generator and the exposing switch can be attached/detached via only one surface of each of housings thereof.

In the aforementioned embodiment, the exposing switch 30 is configured to be fitted into the concave section 40 formed on the housing of the radiation generator 10; however, as illustrated in FIG. 13, instead of forming the concave section 40 on the radiation generator 10, the radiation generator 10 and the exposing switch 30 may be configured to be attachable/detachable to and from each other via only one surface of each of the housings thereof. Such a configuration enables attaching/detaching of the exposing switch 30 with respect to the radiation generator 10 to be performed more easily.

Figure 14:
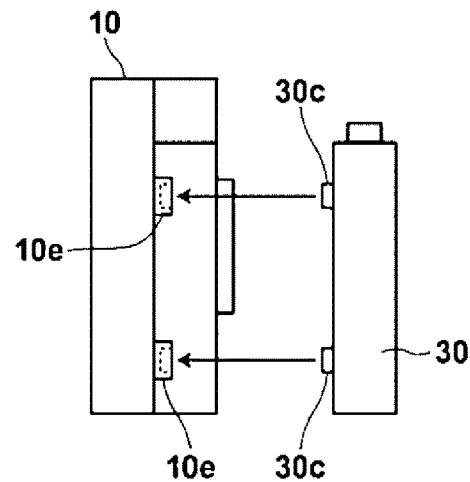
FIG. 14 illustrates a situation in which attaching/detaching surfaces of the radiation generator and the exposing switch are curved surfaces.

In addition, as illustrated in FIG. 14, the attaching/detaching surfaces of the radiation generator 10 and the exposing switch 30 may be curved surfaces.

In the present embodiment, the magnets are used to configure such that the radiation generator 10 and the detachable portion 20 can be attached/detached to and from each other; however, as with the exposing switch 30, a member, such as a hook-and-loop fastener, having adhesiveness may be disposed to thereby provide an attachable/detachable configuration, or an attachable/detachable configuration may be provided using a mechanical mechanism.

What is claimed is:

1. A radiation irradiating apparatus comprising:
a radiation generator that generates radiation; and
a switch that controls emission of the radiation from the radiation generator,
wherein the radiation generator and the switch are constituted by separate housings, and
wherein the radiation generator and the switch are attachable and detachable to and from each other via a surface of a portion of each of the housings thereof.

2. The radiation irradiating apparatus according to claim 1,
wherein the housing of the radiation generator has a concave section, and
wherein a surface forming the concave section and a surface of a portion of the housing of the switch each constitute an attaching/detaching surface.

3. The radiation irradiating apparatus according to claim 2, wherein the attaching/detaching surface of the switch has two surfaces orthogonal to each other.

4. The radiation irradiating apparatus according to claim 2, wherein the attaching/detaching surfaces of the radiation generator and the switch are curved surfaces.

5. The radiation irradiating apparatus according to claim 2, wherein the radiation generator and the switch are attachable and detachable to and from each other via only one surface of each of the housings thereof.

6. The radiation irradiating apparatus according to claim 2, wherein, when the switch is attached to the radiation generator, a surface of the housing of the switch, the surface being other than the attaching/detaching surface, is flush with a housing surface of the radiation generator.

7. The radiation irradiating apparatus according to claim 6, wherein at least two mutually orthogonal surfaces of the housing of the switch, the at least two mutually orthogonal surfaces being other than the attaching/detaching surface, are flush with housing surfaces of the radiation generator.

8. The radiation irradiating apparatus according to claim 1, wherein the housing of the switch forms a portion of a surface of a rectangular parallelepiped or a corner thereof in a state in which the switch is attached to the radiation generator.

9. The radiation irradiating apparatus according to claim 1, wherein the radiation generator and the switch are attachable and detachable to and from each other due to a magnet.

10. The radiation irradiating apparatus according to claim 1, wherein the radiation generator and the switch are attachable and detachable to and from each other due to a member having adhesiveness.

11. The radiation irradiating apparatus according to claim 1, wherein the radiation generator and the switch are attachable and detachable to and from each other due to a mechanical configuration.

12. The radiation irradiating apparatus according to claim 1, the radiation irradiating apparatus comprising:
an emission control unit that stops emission of radiation from the radiation generator when the switch is attached to the radiation generator.

13. The radiation irradiating apparatus according to claim 12, the radiation irradiating apparatus comprising:
a detection unit that detects that the switch is attached to the radiation generator.

14. The radiation irradiating apparatus according to claim 13, wherein the detection unit is disposed on each of the attaching/detaching surfaces of the radiation generator and the switch.

15. The radiation irradiating apparatus according to claim 1,
wherein the radiation generator has a battery, and
wherein, when the switch is attached to the radiation generator, a distance from the switch to the battery is longer than a distance from the switch to a radiation source of the radiation generator.

* * * * *